(12) United States Patent
Suau et al.

(10) Patent No.: US 8,778,368 B2
(45) Date of Patent: Jul. 15, 2014

(54) USE OF ACRYLIC COMB COPOLYMERS AS A COLOUR DEVELOPING AGENT IN COSMETIC COMPOSITIONS

(75) Inventors: Jean-Marc Suau, Lucenay (FR); Olivier Guerret, Pern (FR); Renaud Souzy, Caluire et Cuire (FR); Yves Kensicher, Theize (FR)

(73) Assignee: Coatex, Genay (FR)

( * ) Notice: Subject to any disclaimer, the term of this patent is extended or adjusted under 35 U.S.C. 154(b) by 268 days.

(21) Appl. No.: 13/456,438

(22) Filed: Apr. 26, 2012

(65) Prior Publication Data
US 2012/0276032 A1 Nov. 1, 2012

Related U.S. Application Data

(60) Provisional application No. 61/482,392, filed on May 4, 2011.

(30) Foreign Application Priority Data

Apr. 26, 2011 (FR) ...................................... 11 53538

(51) Int. Cl.
*A61K 9/00* (2006.01)
(52) U.S. Cl.
USPC ................... 424/401; 424/61; 424/63; 424/64
(58) Field of Classification Search
CPC ............. A61Q 1/02; A61Q 1/04; A61Q 1/08; A61Q 1/10; A61Q 1/12
See application file for complete search history.

(56) References Cited

U.S. PATENT DOCUMENTS

| 2002/0187173 A1 | 12/2002 | L'Alloret et al. |
| 2005/0008605 A1 | 1/2005 | L'Alloret |

FOREIGN PATENT DOCUMENTS

| AU | 2003250199 A1 | 2/2004 |
| EP | 1 493 774 A2 | 1/2005 |
| EP | 2 147 901 A1 | 1/2010 |
| FR | 2 819 397 | 7/2002 |
| FR | 2 842 415 | 1/2004 |
| WO | WO 02/083594 A1 | 10/2002 |
| WO | WO 2004/006872 A1 | 1/2004 |

OTHER PUBLICATIONS

U.S. Appl. No. 13/411,809, filed Mar. 5, 2012, Souzy, et al.
U.S. Appl. No. 13/415,001, filed Mar. 8, 2012, Suau, et al.
U.S. Appl. No. 13/413,719, filed Mar. 7, 2012, Souzy, et al.

*Primary Examiner* — James Rogers
(74) *Attorney, Agent, or Firm* — Oblon, Spivak, McClelland, Maier & Neustadt, L.L.P.

(57) ABSTRACT

Cosmetic compositions for make-up containing acrylic comb copolymers having the advantage of increasing the intensity of the color produced by these compositions when they are applied to the skin or to keratin derivatives such as the hair or the eyelashes. Not only are the aesthetic properties conferred by these compositions thus improved, but their useful life is also increased, since they allow access to the desired shade (and good intensity) right from the first application.

20 Claims, No Drawings

USE OF ACRYLIC COMB COPOLYMERS AS A COLOUR DEVELOPING AGENT IN COSMETIC COMPOSITIONS

REFERENCE TO PRIOR APPLICATIONS

This application claims priority to U.S. provisional application Ser. No. 61/482,392, filed May 4, 2011; and to French patent application 11 53538, filed Apr. 26, 2011, both incorporated herein by reference.

GENERAL FIELD

One aspect of the present invention is the use in cosmetic compositions for make-up of certain comb copolymers. They have the advantage of increasing the intensity of the color produced by these compositions when applied to the skin or to keratin derivatives such as the eyelashes and hair.

In practical terms, a more marked coloring is observed, i.e., one that is more intense at the level of the surface on which the compositions of the invention are applied. Not only is there an improvement in the aesthetic properties conferred on the skin or the eyelashes, but the useful life of such compositions is increased, since they lead to the desired tint, (and to a good intensity) right from the first application.

Additional aspects, advantages and other features of the present invention will be set forth in part in the description that follows and in part will become apparent to those having ordinary skill in the art upon examination of the following or may be learned from the practice of the present invention. Various aspects, advantages and other features of the present invention may be realized and obtained as particularly pointed out in the appended claims. As will be understood, the present invention is capable of other and different embodiments, and its several details are capable of modifications in various respects, all without departing from the present invention. The description is to be regarded as illustrative in nature, and not as restrictive.

BACKGROUND

Makeup compositions are products such as a foundation, an eye shadow, a blush, an eye liner, an anti-eye-ring product, a body makeup product, a lip makeup product, a mascara, etc. In addition to a fat phase and an aqueous phase, this type of composition generally contains organic or mineral fillers and coloring agents as well as various other potential additives such as surfactants, a film-forming polymer, etc.

In addition to the dermatological virtues of such compositions, their primary purpose is to provide aesthetic properties at the level of the body surface to which they are applied. It may be to eliminate certain skin defects, to lighten or darken it, give a particular shade or shades. In most cases, the coloring obtained, and especially the intensity of this color is a determining factor in describing the quality of a product such as a foundation.

In addition to the satisfaction of the end user who gets the shade desired, the ability to deliver the desired color with maximum intensity right from the first application will impact the useful life of the product: through a single application, the consumption of the product is reduced.

For such a composition which contains coloring agents as explained above, the intensity of the color delivered at the level of the surface of the skin or eyelashes is reflected in an indirect way through the magnitude L, the first coordinate in the colorimetric standard well known to the person skilled in the art, (L, a, b) as defined by the International Commission on Illumination (ICI).

L defines the brightness, which ranges from 0 (black) to 100 (white). Therefore, for a given hue such as that supplied by pigments, fillers and coloring agents, the higher the value of L, the more the color is attenuated, because it tends toward white. Conversely, a low value of L is associated with a more pronounced coloration, i.e., one that is more intense. The value of L is determined in this Application on a cosmetic composition as such, or on the film resulting from the application of such a composition.

DETAILED DESCRIPTION

Now research by the inventors has brought to light the use of certain "comb" copolymers leading to a large increase in the coloring intensity of cosmetic compositions in which they are introduced.

Here, the expression "comb copolymer" designates a copolymer having a skeleton that is essentially linear and of a (meth)acrylic type on which are grafted at least two side segments constituted of at least one "macromonomer". The term "macromonomer" refers to a polymer or copolymer having at least one terminal group with an unsaturated ethylene function.

In the present invention, the function of this copolymer will be designated by means of the expression "color developer" agent. This implies that the intensity of the tint produced by a cosmetic composition incorporating such a copolymer at the level of the epidermis, the eyelashes or hair, is increased compared to the same composition that does not contain such a copolymer. And it is noted that in the present application, the measurement of this color intensity will always be done indirectly by means of the value of the parameter L (either of the cosmetic composition per se, or after its application in the form of a film).

A preferred macromonomer covered by the present invention has the formula (I):

$$R\text{—}(PO)_m\text{-}(EO)_n\text{—}R' \qquad (I)$$

m and n are integers that are less than 150, with at least one being a non-zero, PO and EO respectively designate propylene oxide and ethylene oxide, R designates a polymerizable unsaturated function, R' represents hydrogen.

The use of comb copolymers is already described in the field of cosmetics, particularly for hair care (EP 1 632 508 A1 and EP 2 168 991 A1). These 2 documents refer to structures that are well known to the person skilled in the art, in which the macromonomer differs from that of the present invention by the fact that R' is necessarily an alkyl group. They feature the specific macromonomers MPEG550 and MPEG2000, respectively methoxypolyethylene glycol methacrylate and methoxypolyethylene glycol, with a mean molar mass by weight equal to 550 g/mol and 2,000 g/mol.

It is shown in this application that surprisingly, because it is not taught or suggested in the state of the art, comb copolymers of the prior art, as described in the above-noted two documents, are not suitable as color developers according to the definition already given. Conversely and surprisingly, the particular choice of the macromonomer with the formula (I) above enables the production of comb copolymers that are very effective in increasing the intensity of the color, such as that produced by a cosmetic composition.

Such a macromonomer with formula (I) is already known and described in U.S. Pat. No. 6,034,208. The manufacture of copolymers incorporating such a macromonomer is also known (see documents U.S. Pat. No. 6,815,513, U.S. Pat. No. 6,214,958, U.S. Pat. No. 6,664,360 and U.S. Pat. No. 7,232,875). Finally, another use of these specific structures is already known: as additives in formulations of plaster (EP 1 377 533 A1, EP 1 615 860 A1), of cement (FR 2 939 128 A1 and FR 2 939 428 A1) or in paper coating dispersions (French application not yet published and filed under number FR 10 54575).

In addition, another preferred characteristic of the comb copolymer according to the present invention is its mean molar mass by weight which must be "low", i.e. preferably between 20,000 g/mol and 200,000 g/mol, unlike other comb copolymers described in the prior art and that have a much higher mass (see particularly documents EP 2 162 476 and EP 1 966 441 which reveal masses that are at times greater than 1,000,000 g/mol for comb copolymers incorporating a macromonomer where R' designates the methyl group). Nothing would suggest such a choice in the state of the art to resolve the question of increasing the intensity of the color of a cosmetic composition.

Also, an object of the present invention is the use as a color developing agent in a cosmetic formulation for makeup of at least one (meth)acrylic comb copolymer characterized in that it has:
  a) at least one monomer which is (meth)acrylic acid
  b) and at least one macromonomer with the formula (I):

$$R-(PO)_m-(EO)_n-R' \quad (I)$$

m and n are integers that are less than 150, with at least one being a non-zero,
  PO and EO respectively designate propylene oxide and ethylene oxide,
  R designates a polymerizable unsaturated function,
  R' represents hydrogen.
and in that it presents a mean molar mass by weight of between 20,000 g/mol and 250,000 g/mol.

This use is also characterized in that the (meth)acrylic comb copolymer is constituted, expressed as a percentage by weight of each of its components, of:
  a) 5% to 30%, preferentially from 15% to 25% of at least one monomer which is (meth)acrylic acid,
  b) 70% to 95%, preferentially 75% to 85% of at least a macromonomer with the formula (I),
  c) 0% to 20%, preferentially from 0% to 10% of at least one monomer which is an ester of (meth)acrylic acid, preferentially ethyl acrylate,
  the sum of the percentages a), b), and c) being equal to 100%.

This use is also characterized in that R preferentially designates the methacrylate function.

This use is also characterized in that the (meth)acrylic comb copolymer presents a mean molar mass by weight that is preferentially between 30,000 g/mol and 120,000 g/mol.

In a preferred manner, this use is characterized in that m and n are both non-null, preferentially between 10 and 90.

The (meth)acrylic comb copolymer can be obtained by known processes, and particularly by free radical polymerization in solution, in direct or inverse emulsion, in suspension or precipitation in solvents, in the presence of initiation systems and transfer agents, or even in a controlled radical polymerization and preferentially in polymerization controlled by a nitroxides (NMP) or by cobaloxymes, in polymerization by atom transfer radical polymerization (ATRP), by controlled radical polymerization by sulphur derivatives selected from among the carbamates, dithioesters or trithiocarbonates (RAFT) or the xanthates.

It may be fully or partially neutralized by one or more neutralizing agents with a monovalent or polyvalent cation, the agents being preferentially being selected from ammonium hydroxide or among the hydroxides and/or oxides of calcium, magnesium, or among the hydroxides of sodium, potassium, lithium, or among the primary, secondary or tertiary aliphatic and/or cyclic amines such as preferentially the stearylamine, ethanolamines (mono-, di-, triethanolamine), mono and diethylamine, cyclohexylamine, methylcyclohexylamine, amino methyl propanol, morpholine, and preferentially in that the neutralizing agent is chosen from among triethanolamine and sodium hydroxide.

It can also be separated into several phases according to static or dynamic processes by one or more polar solvents preferentially belonging to the group consisting of water, methanol, ethanol, propanol, isopropanol, the butanols, acetone, tetrahydrofuran or their mixtures.

In this use, the cosmetic composition preferably contains:
  a) 10% to 99.9%, preferentially 15% to 99.5%, very preferentially 20% to 90%, and still more preferentially 50% to 70% by weight with respect to its total weight, of the aqueous phase.
  b) 0.1% to 90%, preferentially 0.5% to 85%, very preferentially 10% to 80%, and still more preferentially 30% to 50% by weight with respect its total weight, of the non-aqueous phase.
  the sum of a)+b) being equal to 100%.

The aqueous phase can form the continuous phase of the composition in question. It can be constituted mainly of water, but may also include a mixture of water and organic solvents that are miscible in water (miscibility in water greater than 50% by weight at 25° C.) and preferentially chosen from the lower mono-alcohols with 1 to 5 carbons such as ethanol, isopropyl alcohol, the glycols with 2 to 8 carbon atoms such as propylene glycol, ethylene glycol, 1,3-butylene glycol, dipropylene glycol, the C3-C4 ketones, the C2-C4 aldehydes and the ethoxylated alcohols.

The fat phase is composed of natural or synthetic bodies that are non-miscible in water, liquid at room temperature (25° C.) and/or solid at room temperature and chosen preferentially from among the waxes, pasty fats, gums and their mixtures. These fats can be of animal, vegetable, mineral or synthetic origin. In addition, the aqueous phase may contain lipophilic organic solvents.

This formulation is also characterized in that it includes from 0.05% to 10%, preferably 0.05% to 5%, more preferably 0.05% to 2%, and even better, 0.1% to 1% by dry weight with respect to its total weight, of the comb copolymer.

This composition is also characterized in that it contains coloring agents and/or reflective particles and/or fillers commonly used in cosmetic compositions.

The coloring agents may be present in the composition, with a content of 0.5% to 30% by weight, preferentially from 2% to 20% by weight, and very preferentially from 5% to 18% by weight with respect to the total weight of the composition.

They can be selected from mineral or organic pigments dye polymers, water-soluble or fat-soluble dyes, organic lacquers, metal powders and their mixtures.

In the meaning of the present invention, reflective particles refers to particles whose size, structure, texture, including the thickness of the layer or layers that constitute them and their physical and chemical nature, and the surface state, allow them to reflect incident light.

The reflective particles can be present in the composition according to the invention at a content of 0.5% to 60% by weight, preferentially from 1% to 30% by weight, and very preferentially from 2% to 20% by weight with respect to the total weight of the composition.

The fillers can be present in the composition according to the invention at 0.1% to 20% by weight, preferentially from 2% to 15% by weight, and very preferentially from 2% to 10% by weight with respect to the total weight of the composition.

This component is also characterized in that it can contain an additional polymer which is a film-forming polymer. According to this invention, a "film-forming polymer" means a polymer capable of forming alone or in the presence of a filmification auxiliary agent, a continuous and adherent film on a support, including on keratinic materials.

This component is also characterized in that it can contain at least one surface active or emulsifying agent.

This composition is also characterized in that it can contain ingredients commonly used in cosmetics, such as vitamins, perfumes, gelling agents, trace elements, softeners, retention aids, alkalinizing or acidifying agents, preservatives, solar filters, antioxidants, propellants, ceramides, foaming agents, emollients, humectants, texture agents, brighteners, anti-aging agents, moisturizing agents, anti-stress and/or soothing agents, dermoprotective agents, or their mixtures.

The composition of the invention can be in the solid form, for example, powdery, compacted or moulded in the shape of a stick, or in the fluid form, for example, a paste or liquid. It can also be in the form of a flexible paste, an ointment, a foam, a serum, or of a solid or fluid cream-type type ointment. For example, it can be a suspension, a single or multiple oil-in-water or water-in-oil emulsion, a gel, particularly an anhydrous one, solid or flexible, and even in the biphasic form.

The composition according to the invention is preferentially selected from a foundation, an eye shadow, a blush, an eye liner, a mascara, an anti-eye-ring product, a makeup product for the body, the lips, the eyelashes, and is preferentially a foundation.

Application of the described compositions to the body, face, hair, lips, nails, skin, eyebrows, eyelashes, etc. by any mechanism, e.g., with the fingers, using an applicator, etc., also makes up a part of the invention.

The composition according to the invention can be manufactured by known processes, generally used in the cosmetic field.

The following examples will allow a better understanding of the invention, without however limiting its scope.

EXAMPLES

A foundation composition is manufactured from the following 4 ingredients (the figures in the last column indicate the weights in grams):

TABLE 1

| | | |
|---|---|---|
| A | A-1 Schercemol ™* 318 Ester (Lubrizol ™) | 5.00 |
| | A-2 Schercemol ™* CO Ester (Lubrizol ™) | 5.00 |
| | A-3 DC 200 ® Fluid (200 cst.)(Dow Corning ™) | 2.00 |
| | A-4 Hydrenol ® MY (Cognis ™) | 2.00 |
| | A-5 Glucate ™* SS Emulsifier (Lubrizol ™) | 1.20 |
| B | B-6 TiO2 Sensient ® W-877 (LCW) | 8.00 |
| | B-7 Iron Oxide Yellow 34-PC-3170 (Emerald Hilton Davis ™) | 0.60 |
| | B-8 Iron Oxide Red 34-PC-3511 (Emerald Hilton Davi ™ s) | 0.20 |
| | B-9 Propylene Glycol | 3.60 |
| | B-10 Butylene Glycol | 2.40 |
| C | C-11 Glucamate ™* SSE-20 (Lubrizol ™) | 1.80 |
| | C-12 Deionized Water | 64.00 |
| D | D-13 Carbopol ®* Aqua SF-1 (Lubrizol ™) | 3.00 |
| | D-14 Triethanolamine (99%) ** | 0.90 |
| | D-15 Glydant Plus ® (Lonza ™) | 0.30 |

First, all the ingredients A are mixed, and the mixture is heated to 50° C.

At the same time, for part B, pigments (B-6, B-7 and B-8) are dispersed in propylene and butylene glycol until a homogeneous phase is obtained.

For part C, Glucate™ SSE-20 is mixed with water and is heated to 50° C.

Then, under agitation, medium B is incorporated gently into medium C. The mixture is heated to 75° C.

Medium A is then added to the formula while maintaining sufficient agitation until a homogeneous medium is obtained. The temperature is maintained at 75° C.

It is then cooled to 60-70° C., and the Carbopol®Aqua SF-1 is added under agitation.

Cooling is continued to 50-60° C., and the medium is neutralized with Triethanolamine (at a pH equal to 6.9).

The formula is cooled to room temperature. Glydant Plus® is then added.

Test No. 1

This test illustrates a reference composition, and does not involve any ingredient in addition to those described in table 1.

Test No. 2

This test demonstrates the prior art and uses a copolymer consisting of, in % by weight of each of its monomers:

a) 1.5% methacrylic acid and 14.5% acrylic acid, b) 84% of a monomer with formula (I):

$$R\text{—}(PO)_m\text{-}(EO)_n\text{—}R' \quad (I)$$

m=0, n=113,

PO and EO respectively designate propylene oxide and ethylene oxide,

R designates the methacrylate function,

R' represents the methyl radical, totally neutralized by sodium hydroxide and with a mean molar mass by weight equal to 30,000 g/mol; macromonomer (I) is thus here the methacrylate of MPEG with a mean molar mass by weight equal to 5,000 g/mol.

Test No. 3

This test illustrates the prior art and uses a copolymer consisting of, in % by weight of each of its monomers:

a) 1.6% methacrylic acid and 6% acrylic acid, b) 92.4% of a macromonomer with formula (I):

$$R\text{—}(PO)_m\text{-}(EO)_n\text{—}R' \quad (I)$$

m=0, n=113,

PO and EO respectively designate propylene oxide and ethylene oxide,

R designates the methacrylate function,

R' represents the methyl radical, totally neutralized by sodium hydroxide and with a mean molar mass by weight equal to 2,300,000 g/mol; macromonomer (I) is thus here the methacrylate of MPEG with a mean molar mass by weight equal to 5,000 g/mol.

Test No. 4

This test illustrates the prior art and uses a copolymer consisting of, in % by weight of each of its monomers:
a) 6% acrylic acid,
b) 94% of a macromonomer with formula (I):

$m=15$, $n=46$,
PO and EO respectively designate propylene oxide and ethylene oxide,
R designates the methacrylate function,
R' represents the hydroxy radical,
totally neutralized by sodium hydroxide and with a mean molar mass by weight equal to 1,500,000 g/mol; macromonomer (I) is thus here the methacrylate of MPEG with a mean molar mass by weight equal to 5,000 g/mol.

Test No. 5

This test illustrates a domain outside of the invention, and implements a compound which is the macromonomer of formula (I):

$m=15$, $n=46$,
PO and EO respectively designate propylene oxide and ethylene oxide,
R designates the methacrylate function,
R' represents the hydroxy radical,
with a mean molar mass by weight equal to 3,000 g/mol; macromonomer (I) is thus here the one used to produce the comb copolymers of the present invention.

Test No. 6

This test illustrates the invention and uses a copolymer consisting of, in % by weight of each of its monomers:
a) 13% acrylic acid,
b) 87% of a monomer with formula (I):

$m=15$, $n=46$,
PO and EO respectively designate propylene oxide and ethylene oxide,
R designates the methacrylate function,
R' represents the hydroxy radical,
totally neutralized by sodium hydroxide and with a mean molar mass by weight equal to 45,000 g/mol.

Test No. 7

This test illustrates the invention and uses a copolymer consisting of, in % by weight of each of its monomers:
a) 7.5% methacrylic acid
b) 92.5% of a monomer with formula (I):

$m=15$, $n=46$,
PO and EO respectively designate propylene oxide and ethylene oxide,
R designates the methacrylate function,
R' represents the hydroxy radical,
totally neutralized by sodium hydroxide and with a mean molar mass by weight equal to 120,000 g/mol.

Test No. 8

This test illustrates the invention and uses a copolymer consisting of, in % by weight of each of its monomers:
a) 14.4% methacrylic acid
b) 85.6% of a monomer with formula (I):

$m=15$, $n=46$,
PO and EO respectively designate propylene oxide and ethylene oxide,
R designates the methacrylate function,
R' represents the hydroxy radical,
totally neutralized by sodium hydroxide and with a mean molar mass by weight equal to 75,000 g/mol.

Optical measurements are carried out on a Dataflash™ 100 Spectrophotometer, equipped with 15 ml glass rounds. By measuring the value of L in the "L, a, b" standard, it is possible to determine the difference in brightness between a sample and a standard. Thus, if dL is positive, the sample is brighter than the standard, and if dL is negative, the sample is darker than the standard. Practically, the apparatus is pre-heated 30 minutes before use. It is calibrated successively with the light trap and the white standard. A cuvette filled with 10 ml of water is placed on the measuring door (measured with a syringe) and then the white standard is placed on the cuvette. A measurement is made as the basis for a standard. Next to be placed on the measuring door are a cuvette filled with 10 ml (measured by syringe) of the composition to be controlled and then the white standard on the cuvette. The measurement is made on the sample to be tested.

TABLE 2

| Test No. | REF/AA/IN | L |
| --- | --- | --- |
| 1 | REF | 22.1 |
| 2 | AA | 24.6 |
| 3 | AA | 25.6 |
| 4 | AA | 24.5 |
| 5 | HI | 25.3 |
| 6 | IN | 20.7 |
| 7 | IN | 20.4 |
| 8 | IN | 20.3 |

The results in Table 2 clearly demonstrate that the double selection on the choice of the macromonomer on the one hand, and the molar mass of the copolymer on the other hand, lead to an increase in the intensity of the color, which was the effect sought.

A set of preferred embodiments are set out below:

1. A make-up composition comprising an aqueous phase, a fat phase, a coloring agent, and a (meth)acrylic comb copolymer comprising, in reacted form:
   a) (meth)acrylic acid, and
   b) a macromonomer of formula (I):

m and n are integers that are less than 150, with at least one being a non-zero,
   PO and EO respectively designate propylene oxide and ethylene oxide,
   R designates a polymerizable unsaturated function,
   R' represents hydrogen.
   said (meth)acrylic comb copolymer having a mean molar mass by weight of 20,000 g/mol-250,000 g/mol,
   wherein said (meth)acrylic comb copolymer is present in said composition in an amount that decreases the value of L for the composition as compared to the same composition without said (meth)acrylic comb copolymer.

2. The composition according to embodiment 1, wherein the (meth)acrylic comb copolymer consists of, by weight in reacted form:
   a) 5% to 30% of (meth)acrylic acid,
   b) 70% to 95% of said macromonomer of formula (I), and
   c) 0% to 20% of an ester of (meth)acrylic acid
   the sum of the percentages a), b), and c) being equal to 100%.

3. The composition according to embodiment 1, wherein R is a methacrylate function.

4. The composition according to embodiment 1, wherein the (meth)acrylic comb copolymer has a mean molar mass by weight of 30,000 g/mol-120,000 g/mol.
5. The composition according to embodiment 1, wherein m and n are each independently 10-90.
6. The composition according to embodiment 1, wherein the copolymer is fully or partially neutralized by one or more neutralizing agents with a monovalent or polyvalent cation.
7. The composition according to embodiment 1, wherein the cosmetic composition comprises 15% to 99.5 by weight with respect to total weight of the aqueous phase and 0.5% to 85 by weight with respect total weight of the fat phase.
8. The composition according to embodiment 1, wherein the aqueous phase comprises a mixture of water and an organic solvent miscible in water.
9. The composition according to embodiment 1, wherein the fat phase comprises natural or synthetic bodies that are non-miscible in water, liquid at room temperature (25° C.) and/or solid at room temperature.
10. The composition according to embodiment 1, comprising 0.05 to 10% by weight, relative to its total weight, of the comb copolymer.
11. The composition according to embodiment 1, wherein the composition further comprises reflective particles and/or a filler.
12. The composition according to embodiment 1, wherein the coloring agent is present in the composition in an amount of 0.5% to 30% by weight with respect to the total weight of the composition.
13. The composition according to embodiment 11, comprising reflective particles in an amount of 0.5% to 60% by weight with respect to the total weight of the composition.
14. The composition according to embodiment 11, comprising a filler in an amount of 0.1% to 20% by weight with respect to the total weight of the composition.
15. The composition according to embodiment 1, wherein the composition further comprises a film-forming polymer.
16. The composition according to embodiment 1, wherein the composition further comprises a surface-active or emulsifying agent.
17. The composition according to embodiment 1, wherein the composition is in a solid, powdery, compacted or moulded form, or in the shape of a stick or in the form of a fluid, a flexible paste, an ointment, a foam, a serum, a cream-type fluid or solid ointment.
18. The composition according to embodiment 1, wherein the composition is a foundation, an eye shadow, a blush, an eye liner, a mascara, an anti-eye-ring product, or a makeup product for the body, the lips, or the eyelashes.
19. The composition according to embodiment 1, wherein the composition is a foundation.
20. A method for increasing the intensity of the color produced by a makeup composition when applied to the skin or to a keratin derivative comprising preparing a makeup composition comprising an aqueous phase, a fat phase, a coloring agent, and a (meth)acrylic comb copolymer comprising, in reacted form:
(meth)acrylic acid, and
a macromonomer of formula (I):

m and n are integers that are less than 150, with at least one being a non-zero,
PO and EO respectively designate propylene oxide and ethylene oxide,
R designates a polymerizable unsaturated function,
R' represents hydrogen
said (meth)acrylic comb copolymer having a mean molar mass by weight of 20,000 g/mol-250,000 g/mol,
wherein said (meth)acrylic comb copolymer is present in said composition in an amount that decreases the value of L for the composition as compared to the same composition without said (meth)acrylic comb copolymer.
21. In a method for formulating a makeup cosmetic composition, the improvement comprising formulating therein an L value-decreasing effective amount of a (meth)acrylic comb copolymer comprising, in reacted form,
(meth)acrylic acid, and
a macromonomer of formula (I):

m and n are integers that are less than 150, with at least one being a non-zero,
PO and EO respectively designate propylene oxide and ethylene oxide,
R designates a polymerizable unsaturated function,
R' represents hydrogen
said (meth)acrylic comb copolymer having a mean molar mass by weight of 20,000 g/mol-250,000 g/mol.
22. A make-up composition comprising a (meth)acrylic comb copolymer comprising, in reacted form:
c) (meth)acrylic acid, and
d) a macromonomer of formula (I):

m and n are integers that are less than 150, with at least one being a non-zero,
PO and EO respectively designate propylene oxide and ethylene oxide,
R designates a polymerizable unsaturated function,
R' represents hydrogen.
said (meth)acrylic comb copolymer having a mean molar mass by weight of 20,000 g/mol-250,000 g/mol.

As used herein the term (meth)acrylic means methacrylic and acrylic, and supports both terms. The terms composed of, contains, containing, and terms similar thereto, when referring to the ingredients, parts, reactants, etc., of a composition, component, etc., mean, in their broadest sense, "includes at least" (i.e., comprises) but also include within their definition all those gradually restricted meanings until and including the point where only the enumerated materials are included (e.g., consisting essentially of and consisting of).

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. The term "mentioned" notes exemplary embodiments, and is not limiting to certain species. As used herein the words "a" and "an" and the like carry the meaning of "one or more."

All references, patents, applications, tests, standards, documents, publications, brochures, texts, articles, etc. mentioned herein are incorporated herein by reference. Where a numerical limit or range is stated, the endpoints are included.

Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A make-up composition comprising an aqueous phase, a fat phase, a coloring agent, and a (meth)acrylic comb copolymer comprising, in reacted form:
   a) (meth)acrylic acid, and
   b) a macromonomer of formula (I):

   $$R—(PO)_m\text{-}(EO)_n—R' \qquad (I)$$

wherein:
   the (meth)acrylic acid forms a main chain and the macromonomer forms a side chain,
   m and n are integers that are less than 150, with at least one being non-zero,
   PO and EO respectively designate propylene oxide and ethylene oxide,
   R designates a polymerizable unsaturated functional group,
   R' represents hydrogen,
   the (meth)acrylic comb copolymer has a mean molar mass by weight in a range of 20,000 g/mol to 250,000 g/mol, and
   the (meth)acrylic comb copolymer is present in the composition in an amount that decreases the value of L for the composition as compared to the same composition without the (meth)acrylic comb copolymer.

2. The composition according to claim 1, wherein the (meth)acrylic comb copolymer consists of, by weight in reacted form:
   a) 5% to 30% of (meth)acrylic acid,
   b) 70% to 95% of the macromonomer of formula (I), and
   c) 0% to 20% of an ester of (meth)acrylic acid,
   where the sum of the percentages a), b), and c) is 100%.

3. The composition according to claim 1, wherein R is a methacrylate functional group.

4. The composition according to claim 1, wherein the (meth)acrylic comb copolymer has a mean molar mass by weight in a range of 30,000 g/mol to 120,000 g/mol.

5. The composition according to claim 1, wherein m and n are each independently from 10 to 90.

6. The composition according to claim 1, wherein the copolymer is fully or partially neutralized by one or more neutralizing agents with a monovalent or polyvalent cation.

7. The composition according to claim 1, comprising 15% to 99.5% by weight of the aqueous phase and 0.5% to 85% by weight of the fat phase, based on the total weight of the composition.

8. The composition according to claim 1, wherein the aqueous phase comprises a mixture of water and an organic solvent miscible in water.

9. The composition according to claim 1, wherein the fat phase comprises natural or synthetic bodies that are non-miscible in water, liquid at a temperature of 25° C. or solid at a temperature of 25° C.

10. The composition according to claim 1, comprising 0.05 to 10% by weight of the comb copolymer, based on a total weight of the composition.

11. The composition according to claim 1, further comprising reflective particles and/or a filler.

12. The composition according to claim 1, comprising the coloring agent in an amount of 0.5% to 30% by weight, based on the total weight of the composition.

13. The composition according to claim 11, comprising the reflective particles in an amount of 0.5% to 60% by weight, based on the total weight of the composition.

14. The composition according to claim 11, comprising the filler in an amount of 0.1% to 20% by weight, based on the total weight of the composition.

15. The composition according to claim 1, further comprising a film-forming polymer.

16. The composition according to claim 1, further comprising a surface-active or emulsifying agent.

17. The composition according to claim 1, in a powdery, compacted or molded form, or in the shape of a stick or in the form of a flexible paste, an ointment, a foam, or a serum.

18. The composition according to claim 1, wherein the composition is a foundation, an eye shadow, a blush, an eye liner, a mascara, or an anti-eye-ring product.

19. The composition according to claim 1, wherein the composition is a foundation.

20. A method comprising applying the composition of claim 1 to the skin or to a keratin derivative.

* * * * *